(12) United States Patent
Shin

(10) Patent No.: US 10,413,190 B2
(45) Date of Patent: Sep. 17, 2019

(54) APPARATUS AND METHOD FOR MEASURING PRESENCE OF ORGANIC MATTER OR LIFE/DEATH OF LIVING MATTER

(71) Applicant: HANBAT NATIONAL UNIVERSITY INDUSTRY-ACADEMIC COOPERATION FOUNDATION, Daejeon (KR)

(72) Inventor: Sang-Mo Shin, Daejeon (KR)

(73) Assignee: Hanbat National University Industry-Academic Cooperation Foundation, Daejeon (KR)

( * ) Notice: Subject to any disclaimer, the term of this patent is extended or adjusted under 35 U.S.C. 154(b) by 315 days.

(21) Appl. No.: 15/536,812

(22) PCT Filed: Dec. 19, 2014

(86) PCT No.: PCT/KR2014/012590
§ 371 (c)(1),
(2) Date: Jun. 16, 2017

(87) PCT Pub. No.: WO2016/098931
PCT Pub. Date: Jun. 23, 2016

(65) Prior Publication Data
US 2018/0000350 A1    Jan. 4, 2018

(30) Foreign Application Priority Data
Dec. 17, 2014  (KR) .................. 10-2014-0182467

(51) Int. Cl.
*A61B 5/00*     (2006.01)
*G01N 21/35*    (2014.01)
(Continued)

(52) U.S. Cl.
CPC .............. *A61B 5/0086* (2013.01); *A61B 5/02* (2013.01); *G01N 21/35* (2013.01); *G01N 33/48* (2013.01); *G01N 2510/00* (2013.01)

(58) Field of Classification Search
CPC ........ A61B 5/0086; A61B 5/02; G01N 21/35; G01N 33/48; G01N 2510/00
(Continued)

(56) References Cited

U.S. PATENT DOCUMENTS

2004/0036002 A1   2/2004  Meisel
2007/0078348 A1*  4/2007  Holman ............... A61B 5/0075
                                                     600/473
(Continued)

FOREIGN PATENT DOCUMENTS

JP          3712132 B2      11/2005
KR     10-2011-0039054 A     4/2011
(Continued)

OTHER PUBLICATIONS

Ryo-taro Yamaguchi et al., "In situ real-time monitoring of apoptosis on leukemia cells by surface infrared spectroscopy", Journal of Applied Physics, 2009, pp. 024701-1~-24701-7, vol. 105.
(Continued)

*Primary Examiner* — David P Porta
*Assistant Examiner* — Gisselle M Gutierrez
(74) *Attorney, Agent, or Firm* — Rabin & Berdo, P.C.

(57) ABSTRACT

This invention relates to an apparatus and a method for measuring whether organic matter is present or whether or not organisms (cells or tissue) are alive using infrared absorption spectroscopic analysis. The measurement apparatus of the invention includes an infrared light source for radiating infrared rays on a sample, an infrared detection unit for detecting the infrared rays transmitted or reflected from the sample, and a determination unit for identifying an
(Continued)

amide infrared absorption peak of the sample using the detected infrared rays and for determining whether organic matter is present or whether organisms are alive or not in the sample using the identified amide infrared absorption peak. In this invention, a reagent is not used, simple measurement is performed, quantification is feasible, and the presence or absence of cells or tissues and changes in the life and death can be consecutively measured for the same sample.

10 Claims, 6 Drawing Sheets

(51) Int. Cl.
  *G01N 33/48* (2006.01)
  *A61B 5/02* (2006.01)
(58) Field of Classification Search
  USPC ..................................................... 250/461.2
  See application file for complete search history.

(56) References Cited

U.S. PATENT DOCUMENTS

2014/0290089 A1    10/2014  Song et al.
2018/0299374 A1*   10/2018  Holman ................ B01L 3/5027

FOREIGN PATENT DOCUMENTS

| KR | 10-2013-0056886 A | 5/2013 |
| KR | 10-1272884 B1 | 6/2013 |
| KR | 10-2014-0117997 A | 10/2014 |
| KR | 10-2014-0130191 A | 11/2014 |
| WO | WO 92/14134 A1 | 8/1992 |

OTHER PUBLICATIONS

Giuseppe Bellisola et al., "Rapid recognition of drug-resistance/sensitivity in leukemic cells by Fourier transform infrared microspectroscopy and unsupervised hierarchical cluster analysis", Analyst, 2013, pp. 3934-3945, vol. 138.
European Search Report dated May 8, 2018.

* cited by examiner

APPARATUS AND METHOD FOR MEASURING PRESENCE OF ORGANIC MATTER OR LIFE/DEATH OF LIVING MATTER

TECHNICAL FIELD

The present invention relates to an apparatus and a method for measuring whether organic matter is present or whether or not organisms are alive. More particularly, the present invention relates to an apparatus and a method for measuring whether organic matter is present or whether or not organisms (cells or tissue) are alive via a simple measurement process using infrared absorption spectroscopic analysis.

BACKGROUND ART

Measuring whether organic matter is present or whether or not organisms are alive is an important part of biology and is key to the development of new drugs or of therapeutic technologies. In a MTT (tetrazolim-based colorimetric) detection method used for measuring apoptosis in biologic laboratories, hospitals, or pharmaceutical companies all over the world, samples may be simply, quickly, and objectively read using microplate reader equipment, and thus the method is extensively used as an apoptosis detection method. A method using XTT or MTS, which is a modified dye of MTT, is also used. In another method, the expression amount of apoptosis-related protein is obtained by separating and dissolving cells to separate proteins using a quantitative apoptosis analysis method for photographing an image formed after fluorescence dyeing to thus quantitatively analyze the absorbance of each cell based on the obtained image, and then by measuring a change in the relative expression amount of a specific protein using a specific protein inspection method (Western blot). A more convenient method is to measure $OD_{600}$, which is mainly used to measure microbial death using an amount of spectral absorption in the 600 nm band.

The typical method for measuring apoptosis has the following drawbacks. A MTT analysis method is an inspection method for measuring the activity of intracellular mitochondria that reduces MTT tetrazolium, which is a yellow water-soluble substrate, into celadon water-insoluble MTT formazan (3-(4,5-dimethylthiazole-2-yl)-2,5-diphenyl-tetrazolium bromide) based on the action of dehydrogenase. The MTT analysis method is widely used for tests for measuring apoptosis and the toxicity of various chemical substances. This technology is frequently used because reproducible optical density can be obtained using a minimum amount of physical treatment. However, when extracellular abiotic factors affect a process for reducing tetrazolium salts, a fatal error may occur in the analysis results. Accordingly, in apoptosis measurement, a costly dyeing reagent is used, and a lot of measurement time and labor are required. In addition, there are problems in that a region to be dyed may depend on a dyeing method and that it is not easy to perform quantification. Particularly, since it is not possible to observe the death process over time in a dyed sample, it is necessary to use an indirect method of manufacturing a plurality of samples and dying the different samples to measure the cell samples over time, rather than using the same sample. Particularly, flow cytometry (FACS) requires irreversible pretreatment, which involves sample labeling using a fluorescent reagent and detachment of adherent cells from the surface of a plate, followed by analysis. Therefore, when monitoring the growth and death processes of adherent cells, inevitable errors may occur to some degree. Finally, when the above-mentioned specific protein detection inspection method is used, there is a drawback in that many samples and experimental procedures must be prepared and performed.

An example of a conventional technology for measuring the state of living organism samples using a spectroscopic method includes Japanese Patent Publication No. 3712132 (entitled "Spectroscopic determination of properties of biological materials"). In this technology, contact with a specific activating agent is performed, and, with respect to the effect of the contact, only whether or not the cell function is improved is confirmed using infrared spectroscopic analysis. However, there is no confirmation of the change of the infrared spectrum associated with apoptosis therein.

In order to overcome the problems with the conventional measurement method and spectroscopic analysis method up to the hilt, the inventors of the present invention have developed an apparatus and a method for measuring whether organic matter is present or whether or not organisms (cells or tissue) are alive according to a simple process using the characteristic whereby an infrared absorption spectrum changes depending on whether organic matter is present or whether or not organisms are alive, thereby accomplishing the present invention.

DOCUMENTS OF RELATED ART

Patent Document (Patent Document 0001) International Patent Publication No. 92/14134 (1992 Aug. 20).
(Patent Document 0002) Korean Patent Registration No. 1272884 (2013 Jun. 3).
(Patent Document 0003) Japanese Patent Publication No. 3712132 (2005 Nov. 2).

DISCLOSURE

Technical Problem

Accordingly, the present invention has been made keeping in mind the above problems occurring in the prior art, and an object of the present invention is to provide a measurement apparatus and a measurement method using no reagent or using a minimum amount of reagent in order to confirm whether or not organisms including cells or tissues are alive.

Another object of the present invention is to provide an apparatus and a method for measuring whether organic matter is present or whether or not organisms are alive via a simple measurement process.

Still another object of the present invention is to provide a measurement apparatus and a measurement method for confirming whether or not organisms are alive and additionally performing quantification.

Yet another object of the present invention is to provide a measurement apparatus and a measurement method for consecutively measuring the cell change process of the same sample.

Technical Solution

In order to accomplish the above objects, the present invention provides an apparatus for measuring whether organic matter is present or whether or not organisms are alive. The apparatus includes an infrared light source for radiating infrared rays on a sample, an infrared detection unit for detecting the infrared rays transmitted through or reflected from the sample, and a determination unit for identifying an amide infrared absorption peak of the sample using the detected infrared rays and for determining whether organic matter is present or whether or not organisms are alive in the sample using the identified amide infrared absorption peak.

Preferably, the amide infrared absorption peak may be at least one infrared absorption peak of amide I, amide II, and amide III infrared absorption peaks of a protein. The organisms may be any one selected from among animals, plants, and microorganisms.

Preferably, the determination unit determines whether the organic matter is present in the sample depending on whether or not an amide infrared absorption peak is present. The determination unit may determine whether or not organisms are alive in the sample using a position of a wave number value of the amide infrared absorption peak. The determination unit may measure the position of the wave number value of the amide infrared absorption peak using a wave number value of a maximum value of the amide infrared absorption peak. Further, the determination unit may determine whether or not organisms are alive in the sample using a change in a wave number value of the amide infrared absorption peak. The amide infrared absorption peak may be identified in a wave number range of 1640 to 1660 $cm^{-1}$, and the amide infrared absorption peak may be identified in a wave number range of 1610 to 1640 $cm^{-1}$ after a predetermined time to check a peak shift, thus determining the change in the wave number value of the amide infrared absorption peak. Further, the determination unit may measure the change in the wave number value of the amide infrared absorption peak using a change in a wave number value of a maximum value of the amide infrared absorption peak. Further, the determination unit may measure the change in the wave number value of the amide infrared absorption peak using a change in an intensity of a specific wave number value of the amide infrared absorption peak.

Preferably, the determination unit identifies the amide infrared absorption peak in a wave number range of 1600 to 1700 $cm^{-1}$. The infrared light source outputs only infrared rays in a wave number range of 1600 to 1700 $cm^{-1}$.

The present invention also provides a method of measuring whether organic matter is present or whether or not organisms are alive. The method includes radiating infrared rays on a sample, detecting the infrared spectrum transmitted or reflected from the sample, identifying an amide infrared absorption peak of the sample using the detected spectrum, and determining whether organic matter is present or whether or not organisms are alive in the sample using the identified amide infrared absorption peak.

Advantageous Effects

According to the present invention, an apparatus and a method for simply measuring whether organic matter is present or whether or not organisms (cells or tissue) are alive without using a reagent are developed, so that quantification is feasible and so that whether or not cells or tissues are present and the life-death change process are consecutively measured for the same sample. Thereby, it is possible to effectively overcome cost, labor consumption, and reproducibility problems, difficulty of quantification, and an impossibility of measurement over time, which have been pointed out as drawbacks with the conventional method.

MODE FOR INVENTION

Hereinafter, the present invention will be described in more detail with reference to Examples. It is to be understood by those skilled in the art that these Examples are for illustrative purposes only and that the scope of the present invention is not construed as being limited by these Examples.

Example 1. Heating of Living Tissue 10 g of each sample of pork meat (retail commercial market, Korea), pig skin (retail commercial market, Korea), and Pollak (retail commercial market, Korea) was prepared and was collected to measure peaks using an infrared absorption spectrometer (Agilent Technologies, USA). Each sample was placed in a laboratory high-temperature reactor (FINEPCR, Korea) and heated at a temperature of 95° C. for 30 minutes. Each heated sample was collected to measure the peaks using the infrared absorption spectrometer (Agilent Technologies, USA).

Figure 3:
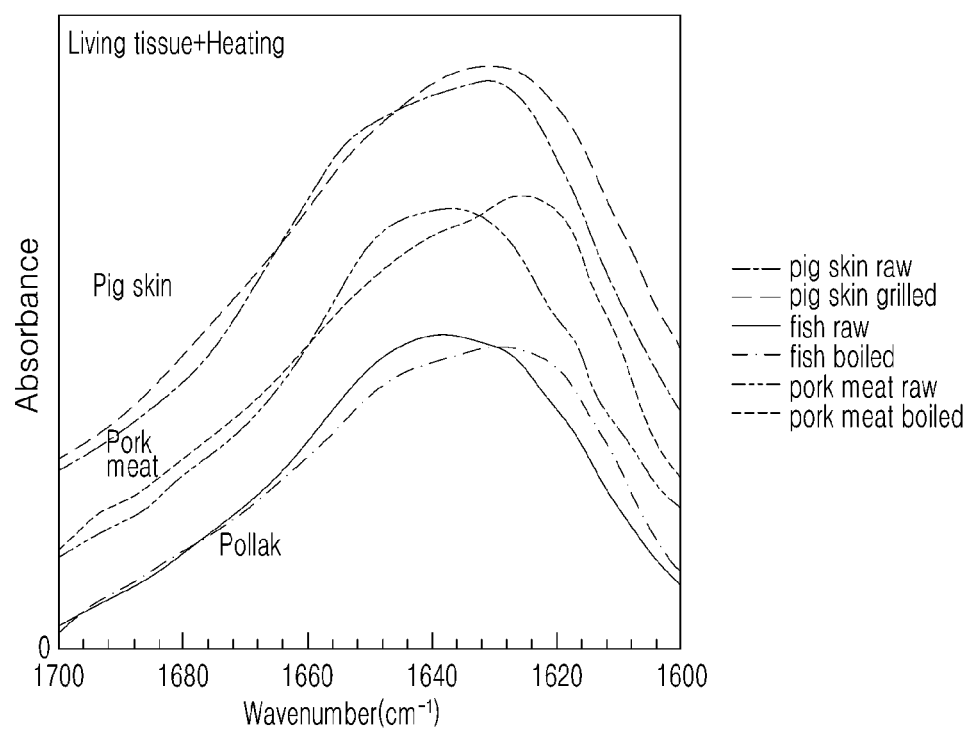
FIG. 3 shows the result of infrared absorption spectroscopic analysis of living tissues of pork meat, pig skin, and Pollack samples after heating.

From FIG. 3, it was confirmed that when the pork meat sample was heated, the peak was shifted from an α-helix rich wave number to a β-sheet rich wave number. In the case of the pig skin sample, it was confirmed that the amide I peak had already been shifted before heating, and that the range of peak shift was narrower in the pig skin sample than in the pork meat sample. In the case of the Pollack sample, it was confirmed that the amide I peak was shifted, as in the case of the above-mentioned pork meat sample, which means that there is a similarity in the processes of protein change in the fish Pollack and the land mammalian pork meat.

Infrared rays do not have sufficiently large energy to cause the electron transition that has been noted for ultraviolet and visible rays. Therefore, the absorption of infrared rays occurs limitedly only in molecular chemical species having small energy differences between various vibration and rotation states. In order to absorb the infrared rays, the molecules must undergo a net change in the dipole moment resulting from vibration and rotational motions. With respect thereto, the alternating magnetic field of the radiation interacts with the molecules and changes the amplitude of one of the motions. The dipole moment depends on a charge difference between two charge centers and the magnitude of the distance therebetween. When a molecule vibrates, periodic changes of the dipole moment occur, and a field that interacts with the electric field of the radiation is established. When the frequency of the radiation exactly coincides with the natural frequency of the molecule, a net transition of energy occurs, which changes the amplitude of the molecular vibration. Accordingly, the absorption of radiation occurs. Similarly, the rotation of asymmetric molecules around the mass center causes periodic dipole changes that may interact with the radiation.

An infrared absorption analysis method is mainly used in order to confirm one kind of purified protein secondary structure (mainly α-helix and β-sheet). The composition ratio of the secondary structure may be confirmed using the morphological change or deconvolution of the amide I peak (wave number of 1600 to 1700 $cm^{-1}$) in the obtained spectra. In the present invention, cultured cells or living tissues, rather than a single kind of protein, are subjected to infrared absorption analysis and the amide peak I is analyzed, thereby verifying that the form of the amide peak I is changed or the position thereof is shifted depending on the death of cells or tissues. Based on this, the death of cells or tissues may be measured.

The sample for infrared analysis is in a gaseous, liquid, or solid state. The container of the gas for infrared rays may be manufactured using a cylinder including NaCl, KBr, and $CaF_2$. The liquid sample may be measured by providing thin films of pure liquid or by injecting liquid between the plates of NaCl, KBr and $CaF_2$. The sample container for infrared rays must not come into contact with water. In order to measure the solid sample, pressure is applied to the sample to form a KBr tablet, or the sample is shaped together with a liquid having a high molecular weight into a paste. The sample container for infrared measurement has a short optical path transmission length, and the infrared absorption band has a relatively small molar extinction coefficient. Therefore, in order to obtain a measurable absorbance, it is preferable to use a solution including an absorption component at a high concentration. The measured concentration depends on the sample, and a concentration of about 0.5 to 10% may be used, without being limited thereto, in order to measure the infrared spectrum.

Example 2. Killing of *Escherichia coli* by Heating and Administration of Antibiotics (Ampicillin)

A. Killing of *Escherichia coli* Cell Line by Heating

A LB (Luria-Bertani) medium was inoculated with *Escherichia coli* (ATCC 25922, Diagnosis and Test Laboratory in Cheonnam National University Hwasoon Hospital, Korea), followed by incubation at 37° C. for 16 to 18 hours. The samples were then collected to measure peaks using an infrared absorption spectrometer (Agilent Technologies, USA). The samples were placed in a high-pressure steam sterilizer (JEIO TECH, Korea) and sterilized by heating at a temperature of 121° C. for 15 minutes. After the heat sterilization is finished, each sample was collected to measure the peaks using an infrared absorption spectrometer (Agilent Technologies, USA).

B. Administration of Ampicillin to *Escherichia coli* Cell Line

A LB medium was inoculated with *Escherichia coli* (ATCC 25922, Diagnosis and Test Laboratory in Cheonnam National University Hwasoon Hospital, Korea), followed by incubation at 37° C. for 16 to 18 hours. The samples were then collected to measure peaks using an infrared absorption spectrometer (Agilent Technologies, USA). The samples were treated with ampicillin at a concentration of 50 µg/ml in 20 mL of a fresh LB medium. The antibiotic-treated samples were collected to measure peaks using an infrared absorption spectrometer (Agilent Technologies, USA).

Figure 4:
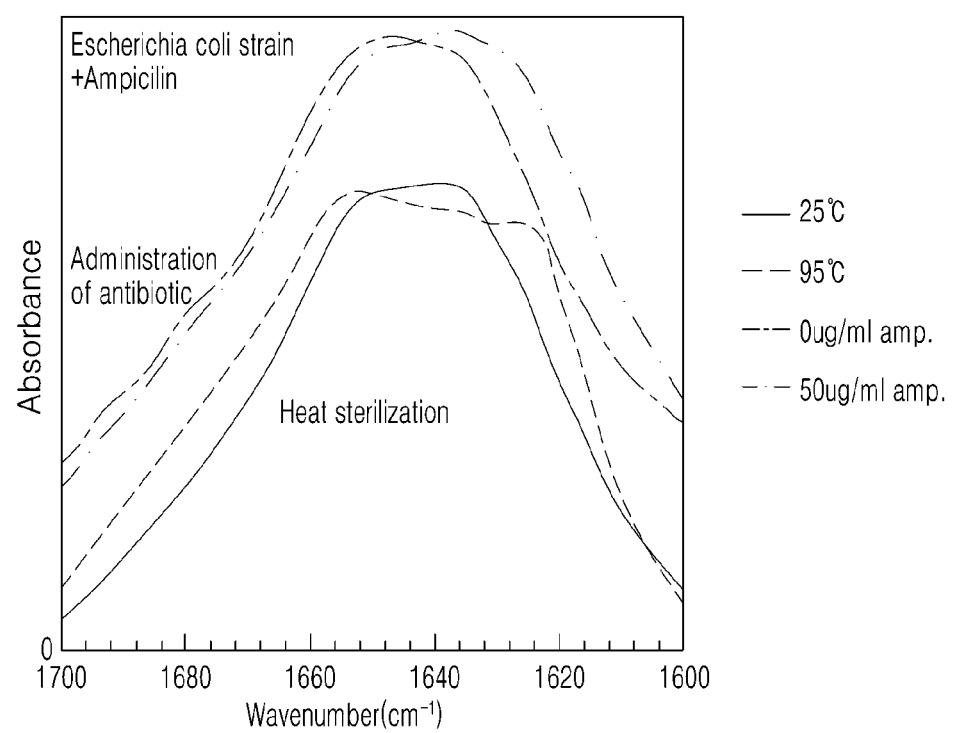
FIG. 4 shows the result of infrared absorption spectroscopic analysis of microbial bacteria samples after microbial bacteria are killed by heating and antibiotics are administered to the microbial bacteria.

From FIG. 4, it was confirmed that the amide I peak was shifted when the *Escherichia coli* sample was sterilized by heating. In the case of the *Escherichia coli* sample treated with ampicillin, which is the antibiotic, the shift of the amide I peak was measured even though the peak was not shifted at a level comparable with that in the case of heat sterilization.

Example 3. Heating of Normal, Cancerous, and Malignant Breast Cells

Breast cells were collected from three women in their 30s to 60s who had no breast cancer, who had breast cancer, and who had malignant breast cancer, and the peaks were measured using an infrared absorption spectrometer (Agilent Technologies, USA). Each sample was placed in a laboratory high-temperature reactor (FINEPCR, Korea) and heated at a temperature of 60° C. for 30 minutes. Each heated sample was collected to measure the peaks using an infrared absorption spectrometer (Agilent Technologies, USA).

Figure 5:
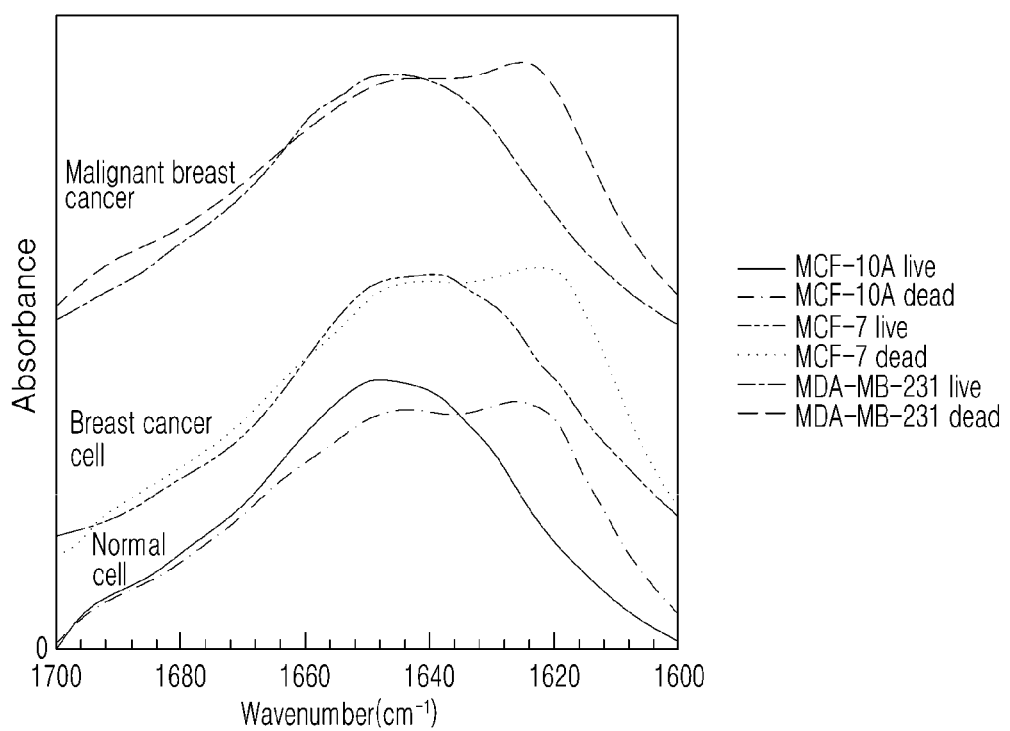
FIG. 5 shows the result of infrared absorption spectroscopic analysis of the samples of normal, cancerous, and malignant breast cells after heating.

From FIG. 5, it was confirmed that when the breast cells were heated, the amide I peak was shifted, as in the results of the heating experiments of Examples 1 and 2.

Example 4. Killing of *Staphylococcus aureus* by Heating and Administration of Antibiotics (Kanamycin)

A. Killing of *Staphylococcus aureus* Cell Line by Heating

A TSB (tryptic soy broth) medium was inoculated with *Staphylococcus aureus* (ATCC29213, Diagnosis and Test Laboratory in Cheonnam National University Hwasoon Hospital, Korea), followed by incubation at 37° C. for 16 to 18 hours. The samples were then collected to measure peaks using an infrared absorption spectrometer (Agilent Technologies, USA). The samples were placed in a high-pressure steam sterilizer (JEIO TECH, Korea) and sterilized by heating at a temperature of 121° C. for 15 minutes. After the heat sterilization is finished, each sample was collected to measure the peaks thereof using an infrared absorption spectrometer (Agilent Technologies, USA) (FIG. 6).

B. Administration of Kanamycin to *Staphylococcus aureus* Cell Line

A TSB medium was inoculated with *Staphylococcus aureus* (ATCC29213, Diagnosis and Test Laboratory in Cheonnam National University Hwasoon Hospital, Korea), followed by incubation at 37° C. for 16 to 18 hours. The samples were then collected to measure peaks using an infrared absorption spectrometer (Agilent Technologies, USA). The samples were divided into two groups and treated with kanamycin at concentrations of 10 µg/ml and 50 µg/ml in 20 ml of a fresh TSB medium. The antibiotic-treated samples were collected to measure the peaks using the infrared absorption spectrometer (Agilent Technologies).

Figure 6:
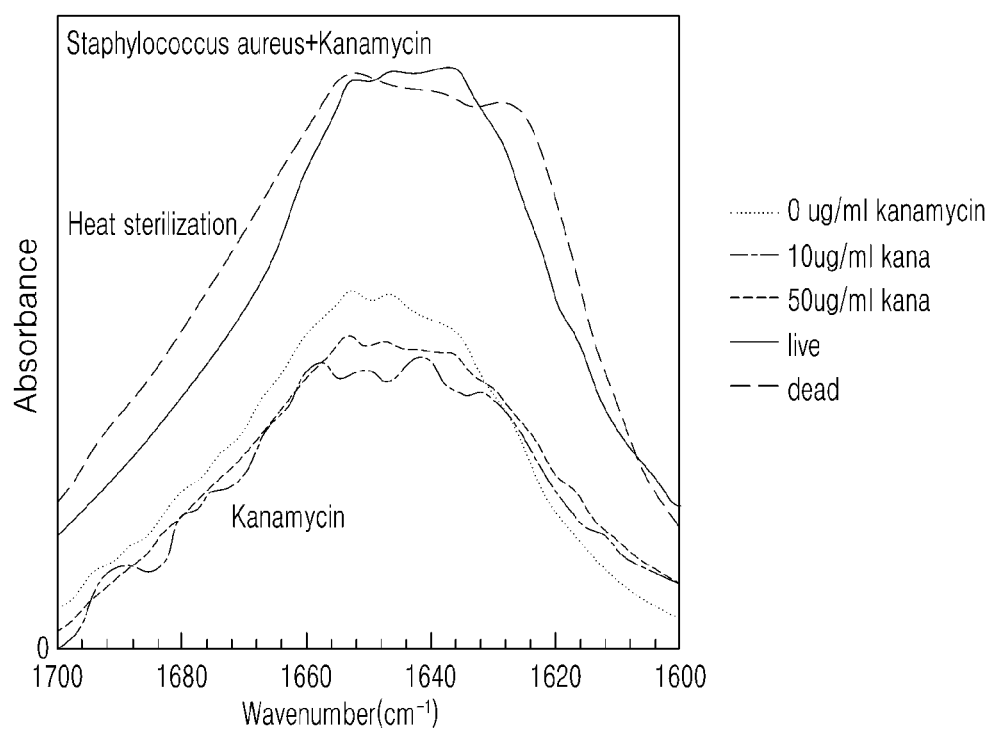
FIG. 6 shows the result of infrared absorption spectroscopy analysis of *Staphylococcus aureus* samples after *Staphylococcus aureus* is killed by heating and is treated with antibiotics (kanamycin)

From FIG. 6, it was confirmed that when the *Staphylococcus aureus* sample was heated, the amide I peak was shifted. In the case of the *Staphylococcus aureus* sample treated with kanamycin, which is the antibiotic, the shift of the amide I peak was not measured, unlike the case of *Escherichia coli* treated with the antibiotics. This is because the antibiotics administered to *Escherichia coli* act to destroy cell membranes while the antibiotics administered to *Staphylococcus aureus* penetrate cells, and accordingly, their action points are different. From the above-described results, it was confirmed that the peak shift was not measured and that the shape of the peak depended on the concentration of administered kanamycin.

Example 5. Administration of Antibiotics (Ampicillin) To *Escherichia coli* Having Antibiotic Resistance/*Escherichia coli* Having No Antibiotic Resistance

*Escherichia coli* cell lines were separated from patients admitted to Cheonnam National University Hwasoon Hospital, and were divided based on whether or not *Escherichia coli* exhibited resistance to ampicillin, which was used as the antibiotic. The samples were treated with ampicillin at a concentration of 50 µg/ml in 20 ml of a fresh LB medium. The antibiotic-treated samples were collected to measure the peaks using an infrared absorption spectrometer (Aglient Technologies, USA).

Figure 7:
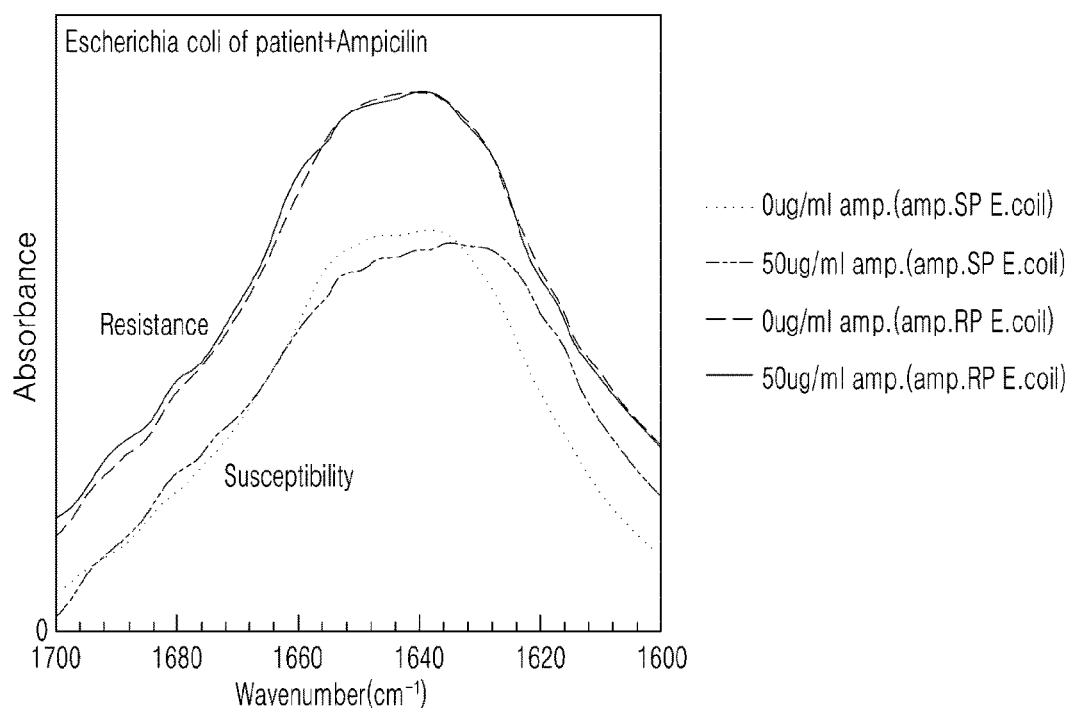
FIG. 7 shows the result of infrared absorption spectroscopy analysis of *Escherichia coli* samples after treatment with antibiotics (ampicillin) against *Escherichia coli* secured from a patient.

From FIG. 7, it was confirmed that the amide I peak was not shifted in the case of the *Escherichia coli* cell line having resistance to ampicillin, which was used as the antibiotic, unlike the case where the *Escherichia coli* samples were sterilized by heating, and that the shift of the amide I peak was measured in the case of the *Escherichia coli* cell line having the susceptibility to the antibiotic ampicillin.

Figure 1:
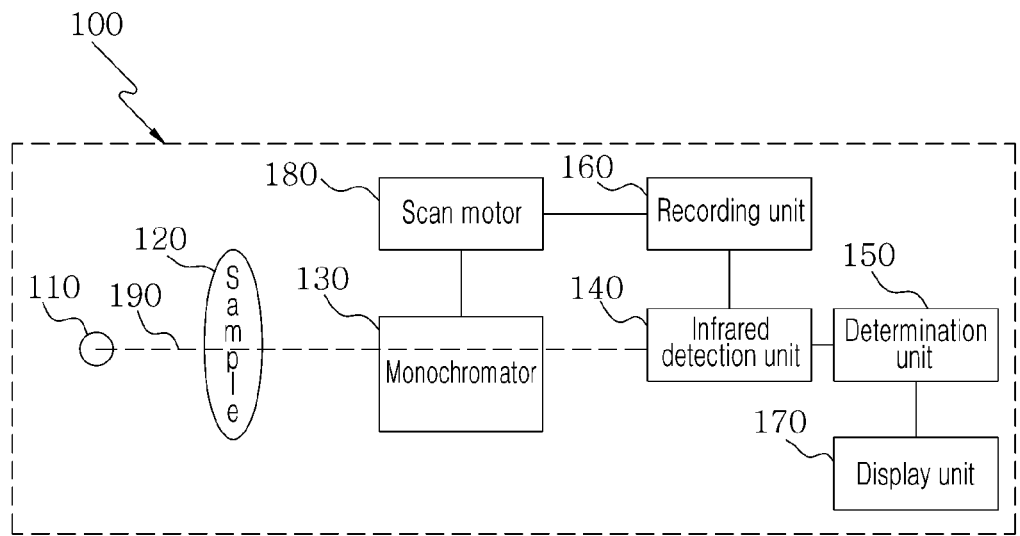
FIG. 1 is a block diagram of a dedicated apparatus for measuring whether organic matter is present or whether or not organisms (cells or tissue) are alive.

Example 6. Constitution of Dedicated Apparatus for Measuring Whether Organic Matter is Present or Whether or not Organisms (Cells or Tissue) are Alive Using Infrared Absorption Spectroscopic Analysis In order to measure whether or not organisms (cells or tissue) are alive in the infrared absorption spectroscopic analysis, a peak long-wavelength shift (red shift) phenomenon, which is the characteristic of the amide peak, particularly the amide I peak, among the absorption peaks of the infrared absorption spectrum may be used. Based on this, a dedicated apparatus 100 for measuring whether organic matter is present or whether or not organisms (cells or tissue) are alive may be constituted as shown in FIG. 1.

In order to perform infrared absorption spectroscopic analysis, an infrared light source 110 for radiating infrared rays on a sample and an infrared detection unit 140 for detecting an infrared spectrum, which is transmitted through or reflected from the sample, are indispensably required. Further, a determination unit 150 for identifying the amide infrared absorption peak of the sample using the detected infrared spectrum and for determining whether organic matter is present or whether or not organisms are alive in the sample using the identified amide infrared absorption peak is required in the dedicated apparatus.

In addition to the essential components, the dedicated apparatus may further include a monochromator 130 for dispersing light emitted from the light source 110 so as to have a limited range of wavelengths and for allowing only radiation having a specific wavelength to selectively reach the infrared detection unit 140, a scan motor 180 connected to the monochromator and a recording unit to perform matching depending on a change in wavelength, a recording unit 160 for measuring and recording the transmittance obtained from the infrared detection unit, a display unit 170 for displaying the infrared detection spectrum, and a sample container 120 containing the sample.

Infrared rays 190 emitted from the infrared light source 110 are transmitted through the sample contained in the sample container 120 or are reflected from the surface thereof, and then pass through the monochromator 130 so that only infrared rays having a specific frequency reach the infrared detection unit 140. The detected infrared data are collected for each frequency to form an infrared absorption spectrum, are displayed on the display unit 170, and are recorded in the recording unit 160. The determination unit 150 identifies the amide infrared absorption peak of the sample in the infrared absorption spectrum, and determines whether organic matter is present or whether or not organisms are alive in the sample using the identified amide infrared absorption peak.

According to the principle of infrared absorption spectroscopic analysis, the dedicated apparatus 100 may adopt a dual beam or a single beam, and may be a dispersive IR absorption spectrometer or an FT (Fourier Transform)-IR absorption spectrometer.

Figure 2:
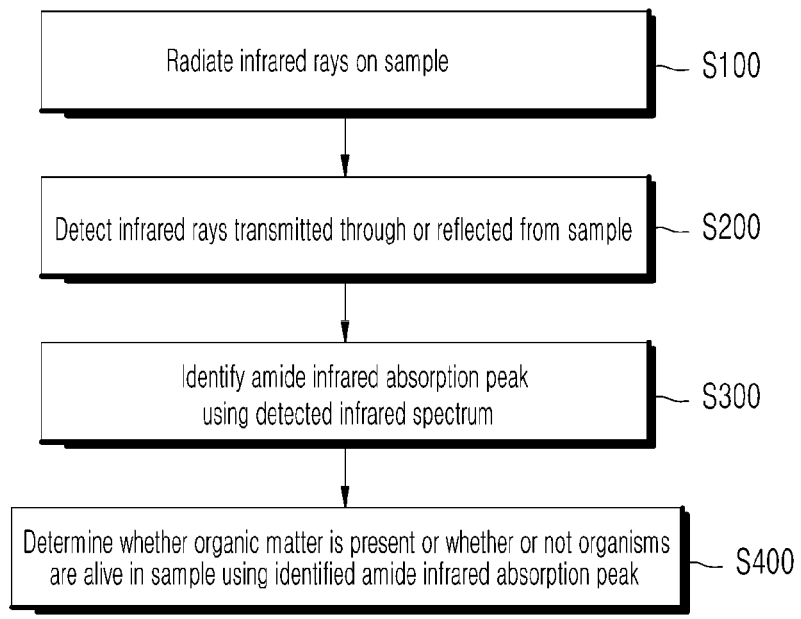
FIG. 2 is a flowchart showing a method of measuring whether organic matter is present or whether or not organisms are alive using the dedicated apparatus or a conventional infrared spectrometer.

As shown in FIG. 2, this process is performed using the dedicated apparatus or the conventional infrared spectrometer via 1) radiating infrared rays on a sample (S100), 2) detecting the infrared rays transmitted through or reflected from the sample (S200), 3) identifying an amide infrared absorption peak using the detected infrared spectrum (S300), and 4) determining whether organic matter is present or whether or not organisms are alive in the sample using the identified amide infrared absorption peak (S400).

A plurality of various functional groups may depend on whether organic matter is present or whether or not organisms (cells or tissue) are alive. However, the amide infrared absorption peak resulting from the amide bond of the tissue protein of organisms is commonly exhibited in all organisms and organic matter containing proteins. The amide peaks have amide I, amide II, and amide III infrared absorption peaks, and all of these peaks change depending on whether organic matter is present or whether or not organisms (cells or tissue) are alive. Particularly, among the peaks, the amide I peak is preferable, and exhibits a shift phenomenon (red shift) in a long-wavelength direction. Accordingly, it is possible to manufacture a dedicated apparatus and to provide a measurement method using the amide I peak.

The characteristics of the amide peaks including the amide I infrared absorption peak (wave number of 1700 to 1600 $cm^{-1}$), the amide II infrared absorption peak (wave number of 1600 to 1500 $cm^{-1}$), and the amide III infrared absorption peak (wave number of 1400 to 1200 $cm^{-1}$) include the position of the wave number value, which is the position of the peak, the magnitude of the wave number value (the reciprocal value of transmittance), and a change in the wave number value over time. The position, the magnitude, and the change in wave number value have respective predetermined values or change direction with respect to each of organic matter and organisms. Based on this, the amount of organic matter or the mortality rate of organisms may be quantitatively measured.

As shown with reference to the above-described Examples, the present invention uses infrared absorption spectroscopic analysis of cells or tissues, and also uses a peak shift phenomenon (red shift) in a long-wavelength direction, which is the characteristic of the amide peak, particularly the amide I peak, among the absorption peaks of the infrared absorption spectrum. Thereby, an apparatus and a method for measuring whether organic matter is present or whether or not organisms (cells or tissue) are alive are provided, thus accomplishing the present invention.

DESCRIPTION OF THE REFERENCE NUMERALS IN THE DRAWINGS

100: Apparatus for measuring whether organic matter is present or whether or not organisms are alive
110: Infrared light source
120: Sample container
130: Monochromator
140: Infrared detection unit
150: Determination unit
160: Recording unit
170: Display unit
180: Scan motor
190: Infrared rays for spectroscopic analysis

The invention claimed is:

1. An apparatus for measuring whether organic matter is present or whether or not organisms are alive using infrared-ray absorption analysis, the apparatus comprising:
an infrared light source for radiating infrared rays on a sample;
an infrared detection unit for detecting the infrared rays transmitted through or reflected from the sample; and
a determination unit for identifying an amide infrared absorption peak of the sample using the detected infrared rays and for determining whether the organic matter is present or whether the organisms are alive or not in the sample using the identified amide infrared absorption peak,
wherein the determination unit determines whether the organic matter is present in the sample depending on whether or not the amide infrared absorption peak is present, and
wherein the determination unit determines whether or not the organisms are alive in the sample using a change in a wave number value of the amide infrared absorption peak.

2. The apparatus of claim 1, wherein the amide infrared absorption peak is at least one of amide I, amide II, and amide III infrared absorption peaks of a protein.

3. The apparatus of claim 1, wherein the determination unit determines whether or not the organisms are alive in the sample using a position of the wave number value of the amide infrared absorption peak.

4. The apparatus of claim 3, wherein the determination unit measures the position of the wave number value of the amide infrared absorption peak using a wave number value of a maximum value of the amide infrared absorption peak.

5. The apparatus of claim 1, wherein the amide infrared absorption peak is identified in a wave number range of 1640 to 1660 $cm^{-1}$, and the amide infrared absorption peak is identified in a wave number range of 1610 to 1640 $cm^{-1}$ after a predetermined time to check a peak shift, thus determining the change in the wave number value of the amide infrared absorption peak.

6. The apparatus of claim 1, wherein the determination unit measures the change in the wave number value of the amide infrared absorption peak using a change in a wave number value of a maximum value of the amide infrared absorption peak.

7. The apparatus of claim 1, wherein the determination unit measures the change in the wave number value of the amide infrared absorption peak using a change in an intensity of a specific wave number value of the amide infrared absorption peak.

8. The apparatus of claim 1, wherein the determination unit identifies the amide infrared absorption peak in a wave number range of 1600 to 1700 $cm^{-1}$.

9. The apparatus of claim 1, wherein the infrared light source outputs only the infrared rays in a wave number range of 1600 to 1700 $cm^{-1}$.

10. A method of measuring whether organic matter is present or whether or not organisms are alive using infrared-ray absorption analysis, the method comprising:
radiating infrared rays on a sample;
detecting the infrared rays transmitted through or reflected from the sample;
identifying an amide infrared absorption peak of the sample using the detected infrared rays; and
determining whether the organic matter is present or whether or not the organisms are alive in the sample using the identified amide infrared absorption peak,
wherein determining whether the organic matter is present in the sample depending on whether or not the amide infrared absorption peak is present, and
wherein determining whether or not the organisms are alive in the sample using a change in a wave number value of the amide infrared absorption peak.

* * * * *